(12) United States Patent
Jordan et al.

(10) Patent No.: US 6,509,174 B2
(45) Date of Patent: *Jan. 21, 2003

(54) CELLS, GENETICALLY MODIFIED WITH OPTICAL MARKER

(75) Inventors: Martin Jordan, Crissier (CH); Florian Maria Wurm, St. Sulpice (CH)

(73) Assignee: Ecole Polytechnique Federal de Lausanne (EPFL), Lausanne (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/098,284

(22) Filed: Jun. 16, 1998

(65) Prior Publication Data

US 2002/0058334 A1 May 16, 2002

(51) Int. Cl.[7] .......................... C12P 21/00; C12N 15/12; C12N 15/67
(52) U.S. Cl. ..................... 435/70.3; 435/69.1; 435/455; 436/72
(58) Field of Search .......................... 435/6, 7.21, 7.2, 435/69.1, 455, 70.3; 424/131.1; 436/172

(56) References Cited

U.S. PATENT DOCUMENTS

| | | | |
|---|---|---|---|
| 5,484,720 A | | 1/1996 | Wurm et al. .............. 435/172.3 |
| 5,686,263 A | | 11/1997 | Wurm ........................ 435/69.1 |
| 5,759,765 A | * | 6/1998 | Harris et al. ..................... 435/4 |
| 5,874,304 A | * | 2/1999 | Zolotukhin et al. ............. 435/6 |
| 5,968,738 A | * | 10/1999 | Anderson et al. ............... 435/6 |

FOREIGN PATENT DOCUMENTS

| | | |
|---|---|---|
| WO | WO 97/26333 | 7/1997 |
| WO | WO 97/42320 | 11/1997 |

OTHER PUBLICATIONS

Ropp et al., "Aequorea Green Fluorescent Protein Analysis by Flow Cytometry" Cytometry vol. 21, pp. 309–317, 1995.*

Hawley–Nelson et al., "LIPOFECTAMINE™ Reagent: A New, Higher Efficiency Polycationic Transfection Reagent" Focus vol. 15(3), p. 73–79, 1993.*

Hawley–Nelson et al., "Lipofectamine Reagent: A new Higher Efficiency Polycationic Liposme Transfection Reagent" Focus vol. 15, pp. 309–317, 1993.*

Gubin, A.N. et al., "Long–Term, Stable Expression of Green Fluorescent Protein in Mammalian Cells," *Biochemical and Biophysical Research Communications*, 236(2):347–350 (1997).

Hanazono, Y. et al., "Green Fluorescent Protein Retroviral Vectors: Low Titer and High Recombination Frequency Suggest a Selective Disadvantage," *Human Gene Therapy*, 8:1313–1319 (1997).

Lybarger, L. et al., "Rapid Generation and Flow Cytometric Analysis of stable GFP–Expressing Cells," *Cytometry*, 25:211–220 (1996).

Wurm, F.M. et al., "Gene Transfer and Amplification in CHO Cells," in *Recombinant DNA Biotechnology III: The Integration of Biological and Engineering Sciences*, vol. 782 of the Annals of the New York Academy of Sciences p. 70–78 (1996).

Wurm, F.M. et al., "Retrotargeting: Use of Defective Retroviral DNA Fragments to Improve Recombinant Protein Production in Mammalian Cells," in *Animal Cell Technology: Products of Today, Prospects For Tomorrow*, Spier, R.E. et al., (Eds.), ESACT, Butterworth–Heinemann, Oxford, pp. 24–29 (1994).

Zhang, G. et al., "An Enhanced Green Fluorescent Protein Allows Sensitive Detection of Gene Transfer in Mammalian Cells," *Biochemical Biophysical Research Communications*, 227(3):707–711 (1996).

Doevendans et al., "The Utility of Fluorescent in Vovo Reporter Genes in Molecular Cardiology," *Biochemical and Biophysical Research Communications*, 222(2):352–358 (1996).

Prasher, "Using GFP to see the light," *Trends in Genetics*, 11(8):320–323 (1995).

* cited by examiner

*Primary Examiner*—John S. Brusca
*Assistant Examiner*—Marjorie A. Moran
(74) *Attorney, Agent, or Firm*—Marshall, Gerstein & Borun (57) ABSTRACT

Fluorescent protein expressing cells with very high fluorescence are described as well as a method to obtain such cells. The fluorescence of such cells can be as high as about 1000 times the auto-fluorescence of the respective host cell. Due to the high fluorescence, said cells are very suitable tools in the development, surveillance and/or optimization of production processes, for selection of culture media and process parameters and for the determination of cell growth and the detection, quantification and monitoring of biomass.

15 Claims, 5 Drawing Sheets

CELLS, GENETICALLY MODIFIED WITH OPTICAL MARKER

BACKGROUND OF THE INVENTION

The present invention concerns a method for obtaining mammalian cells, genetically modified (stably transfected) with a fluorescent marker, preferably green fluorescent protein (GFP), as well as mammalian cells with especially high fluorescence.

The use of fluorescent proteins as reporter molecules for gene expression is already known. One such reporter molecules is the green fluorescent protein (GFP). Said marker protein, originally isolated from the jellyfish *Aequorea victoria* has become an important tool to study gene expression. However, the sensitivity of wild-type GFP has been below that of standard reporter molecules. Thus, to improve the detection of GFP in transfected cells GFP derivatives have been developed, such as chromophore mutations and codon optimization for mammalian cells that make the protein e.g. several times brighter than wild-type GFP (see Zhang G. et. al., *An enhanced green fluorescent protein allows sensitive detection of gene transfer in mammalian cells,* Biochem. Biophys. Res. Commun. 227 (3), 707–711 (1996), WO 97/126333 to the University of Florida Research Foundation, Inc. and WO 97/42320 to The Government of the United States of America).

Despite the proven utility of GFP as a reporter molecule for transient gene expression, there still exist problems with the generation of stably transfected cells giving bright signals (see Hanazono Y. et al., *Green Fluorescent Protein Retroviral Vectors: Low Titer and High Recombination Frequency Suggest a Selection Disadvantage,* Human Gene Therapy 8, 1313–1319 (1997)). The retroviral based method described by Hanazono et al. uses G 418 as a selective drug to isolate stable GFP expressing retroviral producer cell clones, however, the described method was not successful. Gubin A. N. et al. report the successful stable transfection of CHO cells with plasmid DNA encoding both GFP and neomycin phosphor transferase (neo) cassettes (see Gubin A. N. et al., *Long term, stable expression of green fluorescent protein in mammalian cells,* Biochem. Biophys. Res. Commun., 236(2), 347–350 (1997)). One cloned cell line was reported to maintain "high-level" green fluorescence for 18 weeks in G 418 and another 12 weeks in non-selective medium. No growth disadvantage in mammalian cells by GFP expression was observed. Stable GFP expression was also obtained in murine cells (see Lybarger L. et al., *Rapid Generation and Flow Cytometric Analysis of Stable GFP-Expressing Genes,* Cytometry 25, 211–220 (1996)).

The disadvantage of these stably GFP expressing cell lines of the state of the art is their low GFP expression, making them unsuitable for many applications.

BRIEF SUMMARY OF THE INVENTION

A general goal of the present invention is to provide cells, cell lines and/or cell strains, stably expressing fluorescent proteins, that are e.g. producible by the method also being an object of the present invention.

Further objects of the present invention are methods for process development and process optimization wherein the cells/cell lines/cell strains of the present invention are used.

In the following text the term "cells" will be used for cells as well as cell lines and cell strains.

The cells of the present invention are characterized by a fluorescence signal, in particular a fluorescence signal that is at least 100 times the auto-fluorescence of the respective host cell, although preferably at least 200 times higher than said auto-fluorescence and much preferably at least 1000 times said auto-fluorescence. Preferred cells of the present invention are cells, preferably CHO or HEK cells, genetically modified with humanized GFP, in particular those with a fluorescence about 1000 times higher than the auto-fluorescence of the cell.

Suitable proteins for the present invention, herein referred to as "fluorescent proteins", are all optically measurable proteins that can be measured without specific activation, whereby GFP and its derivatives are preferred proteins.

The process for obtaining cells according to the present invention is characterized by a transfection step that is performed in a way to ensure transient transfection efficiencies of at least 25% positive cells, although preferably about 30% or more, and much preferably 50% or more positive cells after 1 day. The term transient transfection, as it is used in connection with the present invention means an initial state of transfection that is a first step to stable transfection, whereby only a small percentage of transiently transfected cells reach the stable state.

The cells of the present invention are—due to their specific features—a very useful tool in process development and optimization making such development and optimization much faster. The fluorescent signal of e.g. GFP can quickly and easily be measured with a standard fluorometer. The signal can be correlated with biomass and/or cell number, extending the application of fluorescent-protein-expressing cells to assays where cell growth is of importance. Information thus obtained allows rapid screening and optimization.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 1 shows a schematic representation for the definition of positive cells using flow cytometry ($\geq 10000$ cells counted, x-axis=relative fluorescence intensity, y-axis= number of cells), whereby

DETAILED DESCRIPTION OF THE INVENTION

The cells of the present invention are characterized by a fluorescence signal, in particular a fluorescence signal that is more than 30 times higher than the auto-fluorescence of the respective host cell.

Already a signal intensity of 1.5 times the auto-fluorescence is a sufficient intensity to distinguish the protein expressing cells from the non-transfected ones and each cell population expressing enough protein to fulfill this condition can be considered for the purposes of the present invention. Thus, the transient transfection of at least 25% means that at least 25% of the cells have a fluorescence that is at least about 1.5 times their auto-fluorescence. Cells of the present invention, however, usually have a fluorescence signal that is at least 100 times higher than the auto-fluorescence of the cell, and in particular said signal is at least 200 times higher. Often the signal obtained is as much as about 1000 times higher than the auto-fluorescence of the respective host cell.

Preferred fluorescent proteins, are green fluorescent protein(GFP), blue fluorescent protein (BFP), or yellow fluorescent protein (YFP). In the examples described herein GFP was used, however, any other fluorescent protein can also be used. The tern GFP comprises the wild type GFP gene and protein as isolated from the jellyfish *Aequorea victoria*, as well as wave-length shifted and host organism adapted forms, such as in particular the so called humanized GFP.

Suitable host cells in particular are immortalized cells, however, primary cells (non-immortalized) can be used as well. Broadly applicable cells such as but not restricted to CHO cells, HEK cells, COS cells, BHK cells, SP2/0 cells, Vero cells, Namalwa cells etc.(all immortalized cells) or MRC5 cells, WI38 cells (non-immortalized cell strains of human origin (human diploid cells)) are preferred.

The process of the present invention is primarily characterized by a very efficient transfection step, i.e. the method used for the creation of stable cells. The transfection is performed in a way to ensure at least 25% transiently transfected cells, preferably at least about 30% transiently transfected cells, and much preferably 50% or more transiently transfected cells, all percentages referring to cells with detectable expression after 1 day.

It is preferred that at least some of the cells have multiple copies of plasmid or DNA molecules, preferably several hundred, much preferably about 1000 copies or more in a transiently transfected state.

Such an efficient transfection can e.g. be obtained by the calcium phosphate method as described in U.S. Pat. No. 5,484,720 to Genentech, South San Francisco, Calif., or by means of a commercially available kit such as for example DOSPER obtainable from Boehringer-Mannheim, Mannheim, Germany, Transfectam® obtainable from Promega Corporation, Madison, Wis., Clonfectine™ obtainable from Clontech, Palo Alto, Calif., ExGen 500 obtainable from Euromedex, Souffel Weyersheim, France, provided that the process is optimized as described below.

The transfection is improved by optimizing the ratio between transfection reagent and DNA. In addition, it is preferred that the cell density is optimized and, furthermore, much preferably the state or the cells at the time of transfection, such as growth rate, viability, adhesion to the plastic surface, cell cycle, membrane properties and medium conditioning are optimized.

Such optimization is e.g. performed by a series of transfections wherein specific parameters are changed while others are kept constant.

On day 0 the cells are transfected according to the transfection method described above. Transfection can be carried out with any vector comprising the fluorescent protein encoding gene under the control of regulatory sequences that are active in the respective host cell. One suitable vector is e.g. the commercially available plasmid pEGFP-N1 (Clontech, Palo Alto, Calif. USA), which expresses a brighter, red-shifted protein compared to the wild-type.

At day 1 (24 hours after transfection) at least 25% of the cells should be positive, preferably about 30% or more, and much preferably about 50% or more.

Positive cells can be identified by all methods and equipment suitably able to detect fluorescence signals, in particular suitably equipped microscopes or flowcytometer equipment.

Definition of a Positive Cell by Microscope

Using a microscope which is equipped with fluorescent filters, positive cells can be easily identified. For e.g. the EGFP, the excitation maximum is at 480 nm while emission is at 510 nm. This pair of wavelengths can be covered by a standard filter set which is used for the popular fluorescent dye fluorescein. Using a filter set for fluorescein, negative cells show no detectable background signal. Positive cells show a green color. All green cells, distinguishable from the black background and from negative cells due to their GFP content (cells with at least 1.5 times their auto-fluorescence), are considered as positive, independent of whether the signal is weak or bright.

Definition of a Positive Cell by Flowcytometry

Figure 1A:
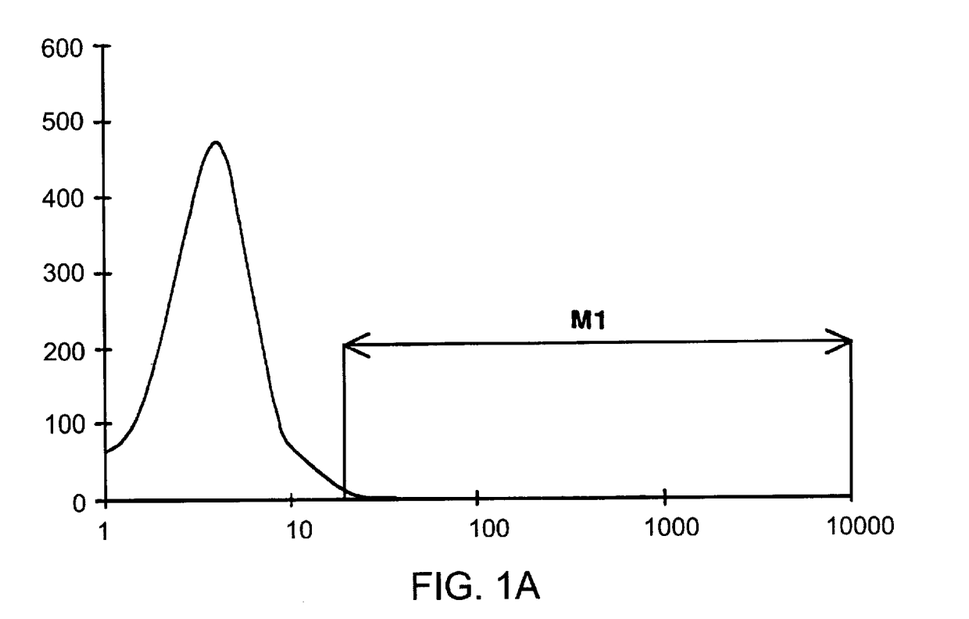
FIG. 1A represents the signal of negative cells and FIG. 1B shows the cells after GFP transfection (40% positive cells).
Figure 1B:
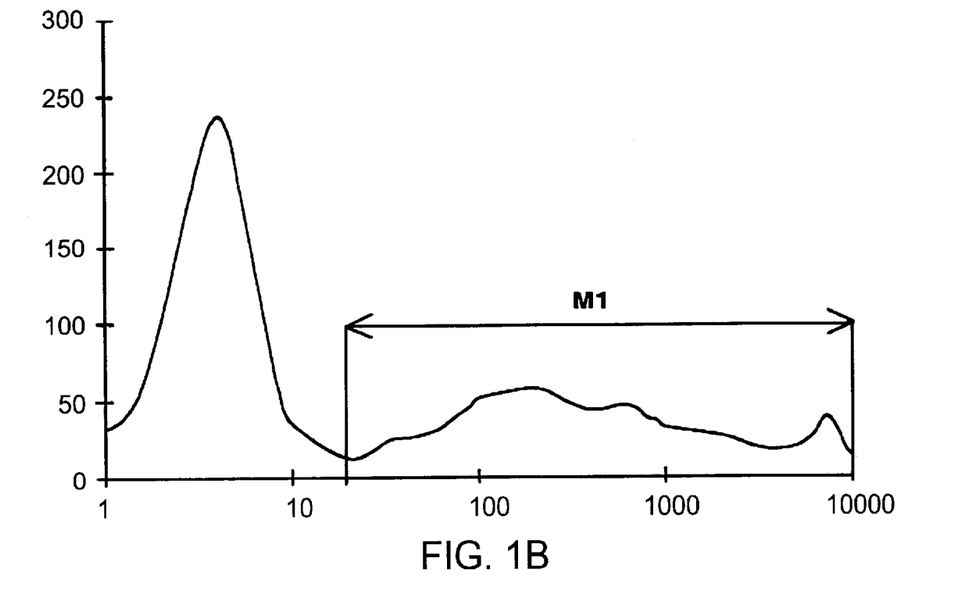

With a flowcytometer machine (such machines are e.g. available from Partec GmbH, Münster, Germany, and Coulter in Hialeah, Fla. USA) the fluorescent signal of individual cells can be measured. The signals are relative and for each measurement (FIG. 1B) a negative control is needed (FIG. 1A). On the horizontal X-axis the signal is plotted at a logarithmic scale ($10^3$ is a signal ten times stronger than $10^2$). The Y-axis indicates the number of cells with a certain signal. Typically, 10,000 cells are analyzed. In order to distinguish negative from positive cells, a group M1 has to be defined, in which for a non-transfected population no cells should be present. In graph two, the peak of negative cells is smaller and a new, broader peak of positive cells appears under M1. It can be seen, that the intensity of positive cells is broadly variable. While the mean signal of negative cells is only 5 fluorescent units, positive cells can give a signal of 10,000 or more fluorescent units.

Most transfected cells loose the plasmid and stop production within a few days after transfection. Only a small fraction will integrate the plasmid into the chromosome and become a stable, producing cell clone.

According to the hitherto applied standard state-of-the-art procedures for isolating fluorescent protein expressing cells, stable clones are isolated using selective drug in order to eliminate non-producers: To obtain individual colonies, the cells are passaged at this stage (a few days after transfection) into plates with larger surface areas using new medium containing the selective drug. Cells need to grow for 10–20 days in the presence of a drug corresponding to the selective marker on the plasmid, until colonies or clones (500–10,000 cells per colony) are visible by the naked eye. The most productive clones obtained by this state-of-the-art method have then to be identified and isolated. In such a process GFP has already been described as a visible marker, however, the individual colonies that were transferred and expanded were not very promising in view of their fluorescent signal intensity.

According to the method of the present invention, however, with a very high transient transfection efficiency extremely bright colonies have been isolated and expanded. In addition, no selective drug is needed to eliminate negative cells. A preferred procedure is about as follows:

The cells are diluted a few days after transfection at a standard ratio, usually 1: 10, without need of any selective pressure. As soon as genetic modification of dividing cells has been obtained, i.e. a state with constant fluorescence to auto-fluorescence ratio (usually after 2–3 more days), clones can be isolated. Under these conditions, usually no colonies are detectable with the naked eye, since the "clones" have only the size of 8–32 cells. Due to the nonselective conditions, most of the cells are negative. However, it was found that this doesn't matter. Under a microscope millions of cells can be visually screened, and the few spots of positive cells can easily be identified. Only a fraction of positive spots emits strong signals, corresponding to bright "clones" of 8–32 cells. The brightest cells among several million cells can then be transferred separately into suitable containers, preferably multiwell plates. This of course is best done under the microscope, using micro manipulation techniques, with all the manipulation controlled under the microscope. This technique allows individual cells or small groups of cells to be loaded into the tip of a pipette, e.g. a 10 μl pipette. The cells can then be transferred into e.g. multiwell plates. It is preferred that a few days later the growth is checked, as well as the presence of negative cells. Such populations, preferably the brightest population, that is at least largely free of any negative cells, can be expanded and established as a new cell line.

This procedure has the advantage that a stable cell line is created without the use of any selective drug. The specific fluorescent signal of an isolated clone, in a preferred case a CHO clone expressing GFP, is about 2000 fold higher than the non-specific background from the parental cell line (determined with a fluorometer by means of a fluorescein filter setup), and in another, much preferred case, is about 10,000 fold higher than said background.

The advantage of the process according to the present invention is that—beside the fact that it allows the isolation of especially bright clones—no marker has to be "sacrificed" to isolate the fluorescent protein expressing clones.

The process of the present invention can of course also be performed with the additional application of drug selection. However, such selective pressure is not necessary. In any case, whether selective pressure is applied or not, it is preferred that selection is performed by either a very stringent selection or an intense screening procedure, eliminating preferably at least 90% of the clones.

It is of course possible and sometimes advantageous to use transfection improving methods such as e.g. the co-transfection of CHO (DHFR⁻) cells with the GFP transfection vector and simultaneously the DHFR/C-type sequence vector as described in Wurm F. M. et al., *Gene Transfer and Amplification in CHO Cells: Efficient Methods for Maximizing Specific Productivity and Assessment of Genetic Consequences,* Recombinant DNA Biotechnology III Vol. 782, Annals New York Academy of Sciences, p. 70–78, (1996); Wurm F. M. et al., *Retrotargeting: Use of defective retroviral DNA fragments to improve recombinant protein production in mammalian cells,* Spier, Griffiths, Berthold, eds.: Animal Cell Technology, Butterwoth-Heinemann, Oxford, p. 24–29, (1994) and U.S. Pat. No. 5,686,263.

The especially bright clones obtainable by the method of the present invention allow several new applications.

One such application is a simplified and more accurate measurement of cell growth, e.g. the establishing of growth curves. Hitherto growth curves were usually obtained by counting cells under a microscope in the presence of try-pan blue. This widely accepted method distinguishes viable cells from dead cells, and distinguishes cells within small aggregates. The reproducibility and the accuracy, however, are limited since the counting is largely dependent on the person performing said counting under the microscope and on the specific sample taken for microscopy. Additionally, for multiple samples, the state-of-the-art method of manually counting is very time consuming.

A faster and more reproducible approach is offered by automatic particle/cell counters where individual particles pass through a capillary, thereby inducing an electrical or optical signal proportional to the diameter of the particle. Such counters normally count all particles, wherefore, in the case of an increasing amount of cell debris and/or cell aggregates, the counting becomes unreliable. Additionally, this method is very time consuming for adherent cells, since the cells have to be brought in suspension for such measurements.

With the cells of the present invention such "counting" and thus the establishing of growth curves can be performed rather quickly, independent from the specific cells (adherent or not), and using the same sample, by simply measuring the optical signal of such sample by suitable apparatuses (e.g. any commercially available fluorometer, such as Cyto Fluor 4000 from Perseptive Biosystems in Framingham, Mass. USA). The optical signal of such genetically modified cells according to the present invention correlates with cell growth as was shown by comparison with growth curves established by classical counting methods (see FIGS. 2 and 3).

The method for establishing growth curves according to the present invention, thus, is not only more accurate but also much faster than the classical counting method.

The cells of the present invention can also be used to select culture media. By measuring the optical signals, significant differences can be observed already within a few hours (see FIG. 3). Although said differences become even greater within a few days, the differences measured within a few hours proved to be sufficiently reliable to allow an accurate analysis. Thus, the cells of the present invention allow a much faster selection of the best culture medium under given conditions.

As it is easily understood, the cells of the present invention are also suitable to determine the best process conditions, such as temperature, dilution factor, time and amount of supplement of specific nutrients/reagents etc.

In view of the extremely strong optical signal of the cells obtained by the method of the present invention and of the cells of the present invention, respectively, a few fluorescent cells can be added to a specific process in order to show changes in the process or in the behavior of the cells, or to get information on the specific state of production, or to optimize said specific process. Already less than 20%, preferably less than 10%, and much preferably less than 5% of e.g. GFP transfected cells according to the present invention have proven to usually be sufficient for such purposes, so that a process can e.g. be performed with about 10–20% of GFP transfected cells and the balance to 100% of e.g. cells producing another protein of interest. The addition of a small amount of fluorescent protein producing cells according to the present invention allows the optimization and surveillance of a large number of different protein production processes, provided that the GFP transfected cells show about the same behaviour as the cells producing the protein to be isolated.

Further applications of the inventive cells are e.g. in tissue engineering, for example for the testing of transplants, such as artificial skin, for tolerability; in toxicology and environmental studies; in drug development, for example, in the search for drugs for cancer therapy; in gene control, and in bio-sensor development.

For some of the above mentioned applications the fluorescent protein expressing gene has to be under the control of a specific promoter activating the fluorescent protein expression under specific conditions only. Such cells are within the scope of the present invention since, under promoter activating conditions they can be isolated as described herein.

Cells or cell cultures, respectively, of the present invention with high fluorescence cannot only be used in applications leading to signal enhancement, but they are also very suitable in applications where a signal reduction shall be measured. Due to the high fluorescence of such cells or cell cultures, respectively, already relatively small changes in the amount of viable, fluorescent protein producing cells are measurable, so that already within a few hours reduction in signal intensity can be observed, thereby providing information on unfavorable environmental conditions, such as the presence of toxic substances. Such unfavorable environmental conditions in cell culture could result in either necrotic or apoptotic mechanisms leading to cell death. Since some of the cell death mechanisms, e.g. apoptosis, are known to be fast processes, first reliable information on the induction thereof can be found by using cells of the present invention within a few minutes.

The above mentioned applications for the cells of the present invention are only examples for possible applications but it has to be understood that the present invention is not limited to these applications.

Thus, the present invention provides methods to detect differences of hitherto impossible resolution in view of time and percentage, it makes cell counting under the microscope or with cell counters superfluous and provides more reliable results in much shorter time.

EXAMPLES

Example 1

Transfection by the Calcium Phosphate Method

The following solutions were prepared:

The Cell Culture Medium

DMEM/F12 powder (#42400, Life Technologies, Basel, CH) was dissolved in water according to the supplier, supplemented with sodium bicarbonate (2.4 g/l) and sterilized by filtration. Sterile fetal calf serum (FCS) was added before using the medium (2% FCS was used as standard, 5% works as well).

Solution A: $CaCl_2$ 250 mM $CaCl_2$ were dissolved in ultra pure $H_2O$ and passed through a 0.2 micrometer sterile filter. This solution is storable in convenient aliquots at room temperature.

Solution B: HEPES-buffer 140 mM NaCl, 50 mM HEPES (N-2-hydroxyethyl-piparazine-N'-2-ethane sulphonic acid) and 1.5 mM $Na_2HPO_4$ were dissolved in ultrapure water. The pH was adjusted to 7.05 (HCl or NaOH). Sterilization was done by filtration. Aliquots were stored at room temperature.

Preparation of CHO and HEK cells for transfection

The CHO cells and the HEK cells used in the following examples were identically prepared.

Exponentially growing cells were diluted to $1 \times 10^5 - 1.5 \times 10^5$ cells per ml. A homogeneous cell suspension was produced and aliquots were added to the wells of multiwell plates. As multiwell plates 24 or 12 well plates were used. The plates were then incubated at 37° C. for 10 to 20 hours.

Transfection

The transfection was performed in that per ml of cell culture 50 $\mu$l of solution A were given in an Eppendorf tube. A total of 2.5 $\mu$g DNA per ml of cell culture (added volume should not exceed 10 $\mu$l) were added. 50 $\mu$l of solution B per ml of cell culture were added to the Eppendorf tube and well mixed (twice with the pipette used). Exactly one minute after mixing, per ml of cell culture 100 $\mu$l of the precipitation cocktail were added to the cell culture at once, in a specific well, and the medium of the cell culture and the precipitation suspension were thoroughly mixed. The plate then was incubated for 4 h at 37° C.

After 1–4 h the precipitate on the cells can be briefly checked under a phase contrast microscope at 200 times magnification. (The plates should not be outside the incubator for too long a period in order to avoid increase of pH.) The precipitate thus obtained was clearly visible, especially on the plastic surface not occupied by cells.

After 4 h the DNA-containing medium was removed and cell culture medium was added. The cells at this point started to express the protein for a few days.

Selection of bright cells or clones, respectively

After 24 hours of incubation, the transient expression of GFP was measured to ensure successful transfection. Only plates showing transient transfection efficiencies of at least 25% positive cells (usually more than 30% of positive cells), were then further cultivated for 6 days at 37° C., whereby, in the case that selective pressure was applied, the culture medium described above was replaced after 2 days (after transfection) with fresh selective culture medium (DMEM/F12 with 2% FCS, and puromycin as the selective drug) and again after 5 days (after transfection) with fresh selective culture medium (DMEM/F12 with 10% FCS supplemented with puromycin) or, in the absence of selective pressure, the cells were diluted 1:10 with fresh non selective medium. After 7 days (after transfection) stable fluorescent protein expressing cell colonies were visible under the microscope. Within 3 more days the colonies became even more readily visible.

Example 2

Isolation of Highly Fluorescent Clones

Homogeneous looking colonies or homogeneous looking parts of colonies were then picked and transferred to multiwell plates containing 1 ml per well of culture medium (DMEM/F12 with 10% FCS, in the case of cells treated with selective pressure optionally supplemented with puromycin). Colonies were located by their fluorescent signal. The tip of a 20 $\mu$"Pipetman" pipette with a volume setting of 10 $\mu$l was brought into contact with the colony which was then gently scraped while also being sucked into the tip by the "Pipetman". The thus picked colony was transferred into a culture medium containing well of a (multi)well plate.

Example 3

Fluorescence Signal Measurement

In order to test the quantification of cells in multiwell plates, using a fluorescent microplate reader (Cyto Fluor 4000 from Perseptive Biosystems in Framingham, Mass. USA), CHO cells suspended in prewarmed (37° C.) phosphate buffered saline (PBS, pH =7.4, #10010 from Life Technologies, Basel) were transferred into a 96 well plate and the fluorescent signals were measured.

Figure 2:
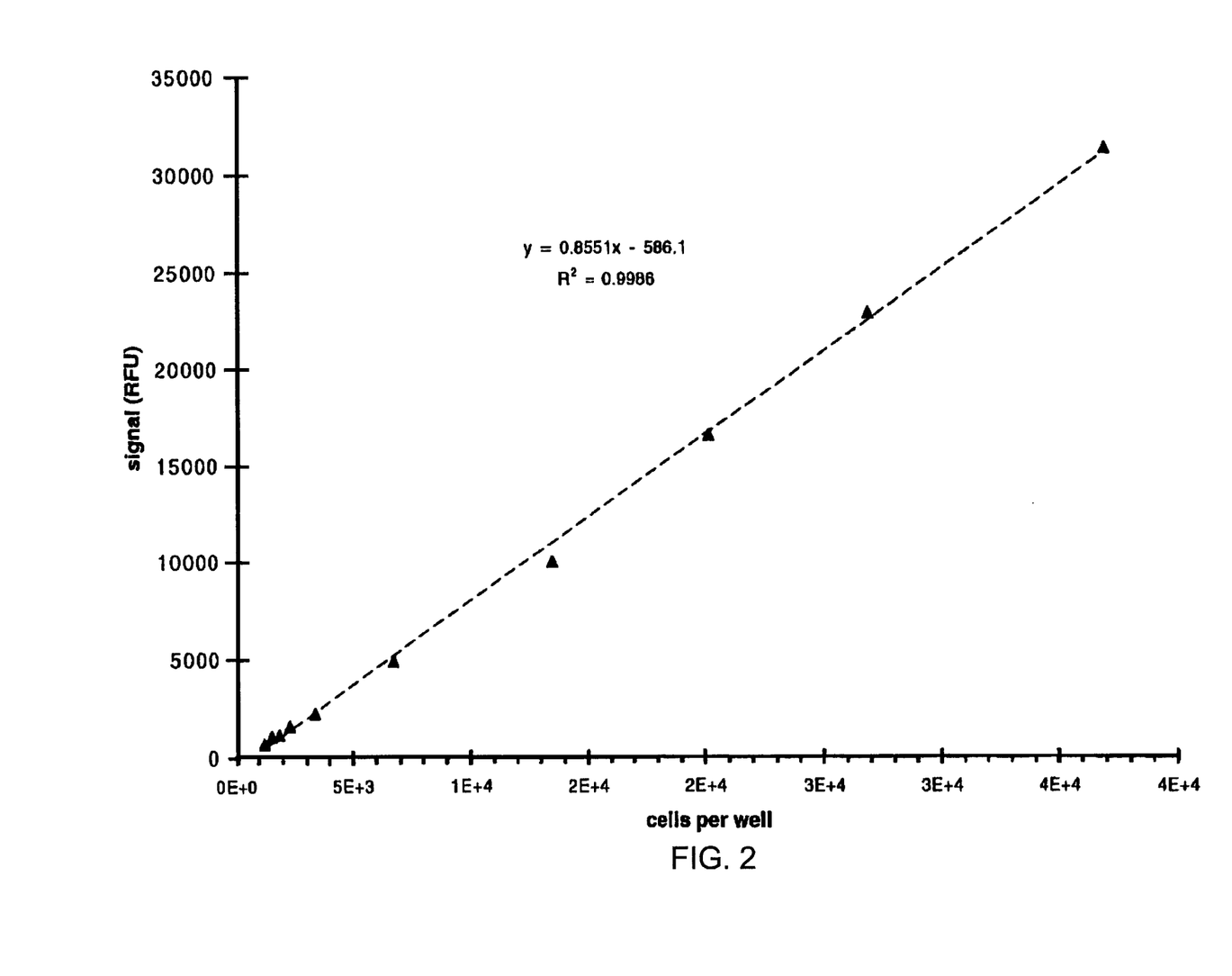
FIG. 2 shows the correlation between the cell number and the fluorescence over the range of confluence.
Figure 3:
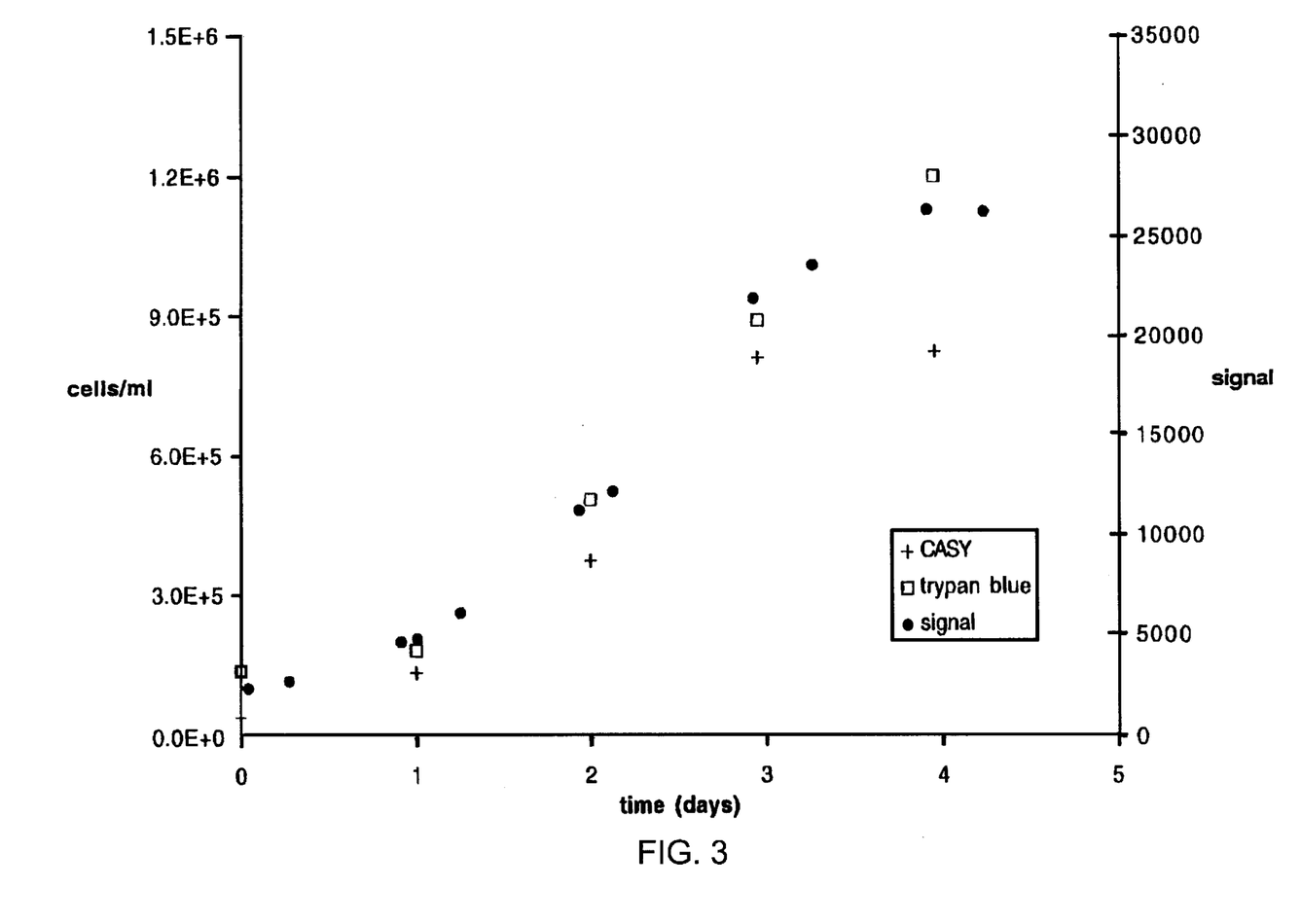
FIG. 3 shows the correlation between the GFP signal and cell growth, wherein the "CASY" marked points refer to automatic cell counting with a CASY™ cell counter, and "trypan blue" refers to manual cell counting under the microscope, and "signal" means the GFP signal.

The volume of PBS added per well was kept constant at 150 µl, while cell concentrations ranged from $1 \times 10^4$/ml PBS to $2.5 \times 10^5$/ml PBS. The temperature was kept at about 37°. The fluorescent signal (average of 6 samples of the 96 well plates) linearly correlates with the amount of CHO cells per well (FIG. 2). Standard errors for multiple samples of the identical cell concentration are below 5%, reflecting an excellent reproducibility of the fluorescent measurement between individual wells. The fluorescent measurement is even more accurate than the dilution of cells, which easily causes errors up to 10%. Since the plotted cell number is based on the factor of dilution, such errors can be seen for data points outside the linear regression (FIG. 2). Having a maximum cell density of $10^6$ cells/ml, the cells can be diluted up to one hundred fold and the signal is still a linear function of cell concentration and can be measured without modification of the fluorescent reader's parameters. At cell concentrations lower than $10^4$ cells/ml, which corresponds to a confluency of 2%, the background coming from the plate becomes significant and the values are less accurate. Having higher cell densities is no problem for the measurement, which indicates that multiple layers of cells do not alter the fluorescent signal. Therefore, over the range of confluence and beyond, the fluorescent signal is a good indicator of cell number.

Example 4

Fluorescence Versus the Trypan Blue Exclusion Method of the State of the Art

The fluorescence of GFP transfected CHO cells was used to establish a growth curve over 5 days. Plates were measured at least twice a day for the GFP values, while 3 wells were harvested every day to determine the cell number using trypan blue. The scales of the axes in FIG. 3 were adapted in order to superpose the curves. The similar shapes of the curves indicate that GFP expression correlates with cell growth.

The fluorescent value was plotted directly. With a calibration (FIG. 2), the fluorescent signal could easily be converted into a cell concentration. Cells were counted before passaging or seeding multiwell plates for new experiments.

As can be seen from FIG. 2, the correlation between cell growth and GFP signal is rather good. Additionally, it was found that GFP transfected CHO cells grew exponentially during the first 4 days.

Example 5

Growth Rate Calculation

Exponentially growing cells were diluted to different physiological seeding densities in standard medium. Growth was monitored by measuring the plate once or several times a day. The maximum fluorescent signal was obtained 3 days after seeding for the highest seeding density and after 7 days for the lowest seeding density. The absolute maximum was slightly higher in the cases with the lower seeding densities. The cells in the plateau phase are viable and the GFP signal remains stable for several days, although showing a slight tendency to decrease.

Very important information can be obtained not only from the plateau phase, but also from the very first day. Plates were repeatedly measured during the period 14–24 hours after seeding. Plotting these early measurements on a logarithmic scale visualized the exponential growth for the different cases. The reproducibility of the measurement proved to be high enough for the growth rate to be determined over a time interval of 10 hours, or even less.

Example 6

Measuring Effects of Changes in the Medium Composition

Figure 4:
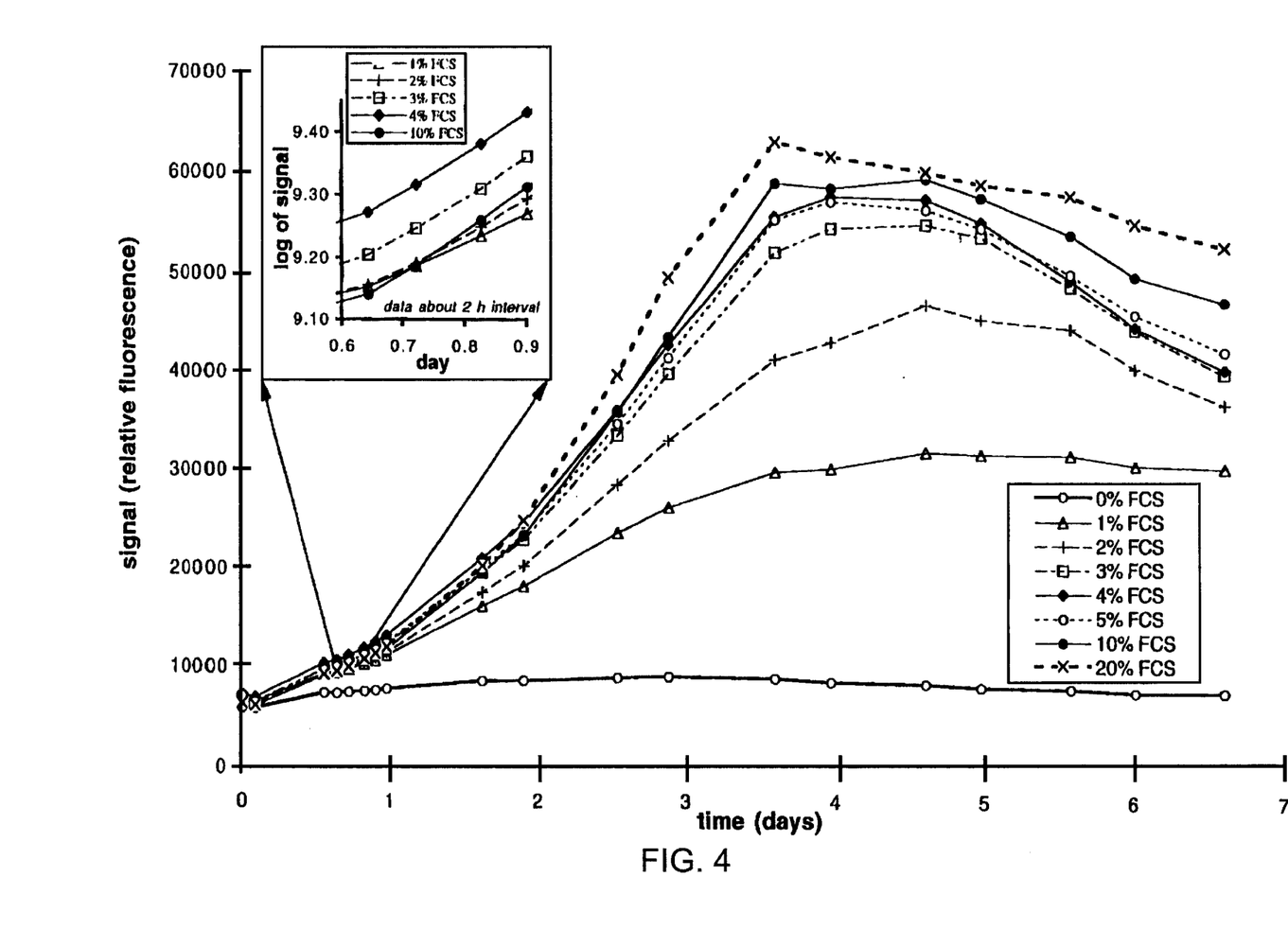
FIG. 4 represents the results obtained by testing different fetal calf serum (FCS) concentrations in a culture medium.

The medium composition was varied in this experiment by changing the concentration of FCS (fetal calf serum). The seeding cell density was kept constant. CHO cells in a pre-culture with 5% FCS were washed with PBS, trypsinized and resuspended in a standard medium without serum. Serum was added, to the final concentrations, to aliquots of this cell solution. In the serum-free samples, no increase in the fluorescent signal could be detected (FIG. 4). Increasing the serum up to 3% clearly stimulated GFP production, while a further increase to 20% did not significantly change the maximum signal. For this experiment a very bright subclone was used (signal 3000 times the auto-fluorescence). Independent from the fluorescent intensity of the subclone, the growth rate calculated for this subclone is comparable to the data of other clones. Again, multiple measurements were made on day one, and the specific growth rate was calculated, exclusively using the values corresponding to the maximum rate. Growth rates obtained on day one already clearly show tendencies which were confirmed by measurements done on the following days. This demonstrates that, using GFP, effects of medium composition can be detected within less than one day by measuring the growth rate, while longer observation can confirm and give additional information about maximum signal and the time needed to achieve the maximum signal.

Example 7

Use of GFP Transfected Cells as a Tool for Process Surveillance

Figure 5:
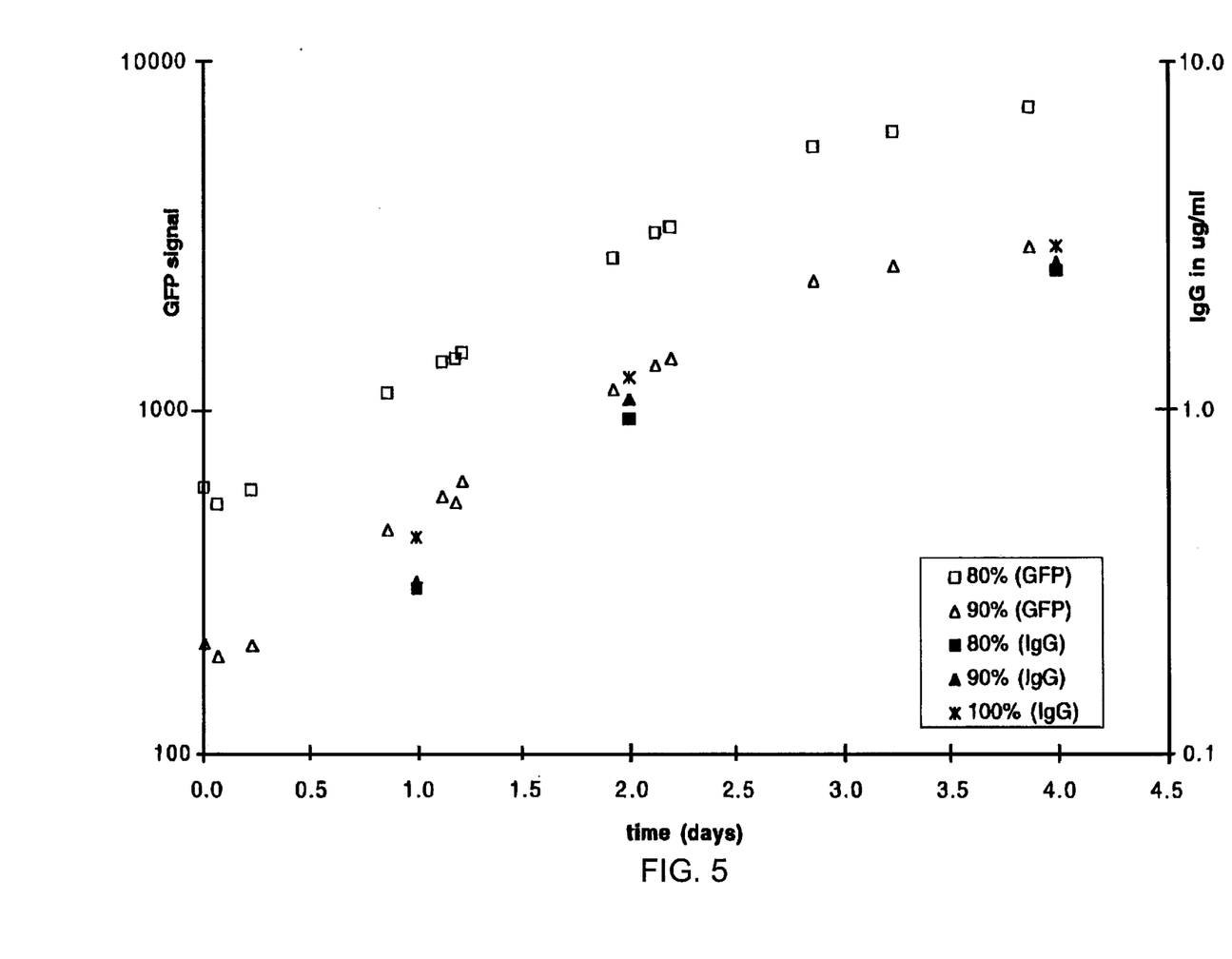
FIG. 5 shows a comparison of GFP signal and IgG (immunoglobulin G) production in mixed cell populations. GFP producing cells were added at the beginning of the experiment, wherein "80%" means 80% IgG producing cells and 20% GFP producing cells, "90%" means 90% IgG producing cells and 10% GFP producing cells, and "100%" means no GFP producing cells added.

A bright clone produced according to the present invention (signal 1400 fold the auto-fluorescence) was used to survey the production of IgG in that 10 or 20%, respectively, of the IgG producing cells were replaced by GFP producing cells. The results are shown in FIG. 5, where the reference (GFP) signifies that the GFP signal was measured and (IgG) refers to the measurement of the IgG concentration. As expected, the intensity of the fluorescent signal correlated with the percentile amount or GFP producing cells added to the production process. The growth behaviour is independent of the small amount of GFP producing cells added, and the starting signal of the 90% curve (10% GFP transfected cells added) shows that even less than 10% GFP transfected cells are sufficient to allow satisfactory surveillance.

While there are shown and described presently preferred embodiments of the invention, it is to be understood that the invention is not limited thereto but may be otherwise variously embodied and practised within the scope of the following claims.

What is claimed is:

1. Clones of mammalian cells genetically modified with a fluorescent protein expressing gene, and expressing a fluorescent protein encoded by said gene wherein the fluorescent protein produces a fluorescent signal which is at least 1000 times higher than the auto-fluorescence of the cells.

2. Cells according to claim 1, wherein the fluorescent protein expressing gene encodes green fluorescent protein (GFP).

3. Cells according to claim 1, wherein the fluorescent protein expressing gene encodes humanized GFP.

4. Cells according to claim 1 which are immortalized cells.

5. Cells according to claim 1, wherein the cells are selected from the group consisting of CHO and HEK cells.

6. A process for obtaining mammalian cells stably transformed with a fluorescent protein expressing gene and expressing a fluorescent protein encoded by said gene wherein the fluorescent protein produces a fluorescent signal, comprising the following steps:

a) transfecting mammalian cells with a fluorescent protein expressing gene wherein mammalian cells are transfected such that at least 25% transient transfection is observed after 24 hours;and b) selecting a clone of mammalian cells stably transformed with a fluorescent protein expressing gene when a state with constant fluorescence to auto-fluorescence is obtained and wherein said cells are genetically modified with a fluorescent protein expressing gene, and expressing a fluorescent protein encoded by said gene wherein the fluorescent protein produces a fluorescent signal which is at least 1000 times higher than the auto-fluorescence of the cells.

7. The process of claim 6, wherein the fluorescent protein expressing gene expresses green fluorescent protein (GFP).

8. The process of claim 6, wherein the fluorescent protein expressing gene encodes humanized green fluorescent protein (GFP).

9. The process of claim 6, wherein the cells are transfected wherein at least 30% transient transfection is observed after 24 hours.

10. The process of claim 6, wherein the cells are transfected wherein at least 50% transient transfection is observed after 24 hours.

11. The process according to claim 6, wherein the transfection is performed wherein cells obtained thereby transiently express at least 1000 copies of plasmid or DNA molecules per cell.

12. The process according to claim 6, wherein the fluorescent clone cells are selected by optical methods.

13. Cells produced according to the process of claim 6.

14. Cells according to claim 1 which are derived from a single clone.

15. A composition comprising a mixture of different clones according to claim 1.

* * * * *